(12) United States Patent
Cantor et al.

(10) Patent No.: US 7,026,287 B2
(45) Date of Patent: Apr. 11, 2006

(54) LECTINS AS ANTI-FIBROTIC AGENTS

(75) Inventors: Jerome Owen Cantor, Brooklyn, NY (US); Bronislava Shteyngart, Brooklyn, NY (US)

(73) Assignee: Jerome O. Cantor, Brooklyn, NY (US)

( * ) Notice: Subject to any disclaimer, the term of this patent is extended or adjusted under 35 U.S.C. 154(b) by 30 days.

(21) Appl. No.: 10/435,549

(22) Filed: May 12, 2003

(65) Prior Publication Data

US 2003/0216300 A1    Nov. 20, 2003

Related U.S. Application Data

(60) Provisional application No. 60/381,367, filed on May 20, 2002.

(51) Int. Cl.
*A61K 38/16* (2006.01)
(52) U.S. Cl. .......................... 514/8; 514/2; 530/387.5; 530/395; 424/725
(58) Field of Classification Search ................ 514/8, 514/2; 424/725; 530/387.5, 39
See application file for complete search history.

(56) References Cited

U.S. PATENT DOCUMENTS

2002/0001600 A1* 1/2002 Oldham et al. ............. 424/401

OTHER PUBLICATIONS

Gabolde et al., J. Med. Genet. 2001, vol. 38, pp. 310-311.*
Garred et al. (Pediatric Pulmonology Mar. 2002, vol. 33, pp. 201-207.*

* cited by examiner

*Primary Examiner*—B. Dell Chism

(57) ABSTRACT

The subject invention is directed to the treatment of tissue fibrosis by administration of an effective amount of lectin. Fibrosis herein refers to the accumulation of extracellular matrix constituents that occurs following trauma, inflammation, tissue repair, immunological reactions, cellular hyperplasia, and neoplasia. Examples of tissue fibrosis include, but are not limited to, pulmonary fibrosis, cirrhosis of the liver, skin scars and keloids, adhesions, fibromatosis, atherosclerosis, and amyloidosis. The treatment is intended for a variety of mammals, including humans.

6 Claims, 6 Drawing Sheets

LECTINS AS ANTI-FIBROTIC AGENTS

This application claim benefit of 60/381,367 filed May 20, 2002.

BACKGROUND

Lectins bind to carbohydrate moieties, e.g. acetylglucosamine, that are ubiquitous in the mammalian extracellular matrix. This suggests the possibility that lectins may be used to coat the matrix and limit further binding of collagen, elastin, and other connective tissue components to carbohydrate groups. The aggregation of large amounts of matrix constituents, as occurs in fibrosis, may therefore be subject to limitation by the introduction of lectins.

This hypothesis was tested in our laboratory. Elastic fiber matrix prepared from cultured rat lung mesothelial cells (1,2) was first treated with tomato lectin (*lycopersicon esculentum*), then covered with hyaluronan (HA), which normally protects the matrix from degradation by elastases. It was found that lectin treatment abolished the protective effect of HA and facilitated breakdown of the elastic fiber matrix by elastase.

Since the binding of HA to the elastic fibers is analogous to fibrosis in that it involves deposition of new matrix material (HA) over existing matrix, the addition of lectin may provide a means of counteracting this process and preventing the formation of scar tissue.

This potential anti-fibrotic activity may not be specific to tomato lectin, but instead be related to a general characteristic of lectins, i.e. binding to carbohydrate moieties. Consequently, lectins, as a class of agents, may prevent the deposition of newly synthesized matrix components, and therefore be useful in treating diseases such as pulmonary fibrosis and cirrhosis of the liver.

SUMMARY OF THE INVENTION

The subject invention is directed to the treatment of tissue fibrosis by administration of an effective amount of lectin. Fibrosis herein refers to the accumulation of extracellular matrix constituents that occurs following trauma, inflammation, tissue repair, immunological reactions, cellular hyperplasia, and neoplasia. Examples of tissue fibrosis include, but are not limited to, pulmonary fibrosis, cirrhosis of the liver, skin scars and keloids, adhesions, fibromatosis, atherosclerosis, and amyloidosis. The treatment is intended for a variety of mammals, including humans.

Lectins which may be administered to treat tissue fibrosis include, but are not limited to, lectins which bind to N-acetylglucosamine, such as chitin-binding lectins and mannose-binding lectins.

Administration of lectins may be performed intratracheally, intravenously, intramuscularly, topically, orally, or by any other route deemed efficacious. The lectin may be administered alone, or with a carrier such as saline solution, DMSO, an alcohol, or water. The lectin may be isolated from a natural source, such as plants or animals, or synthesized by a bioprocess, such as fermentation. The effective daily amount of lectin is from about 10 µg/kg to about 10 mg/kg of body weight.

DETAILED DESCRIPTION OF THE INVENTION

Figure 1:
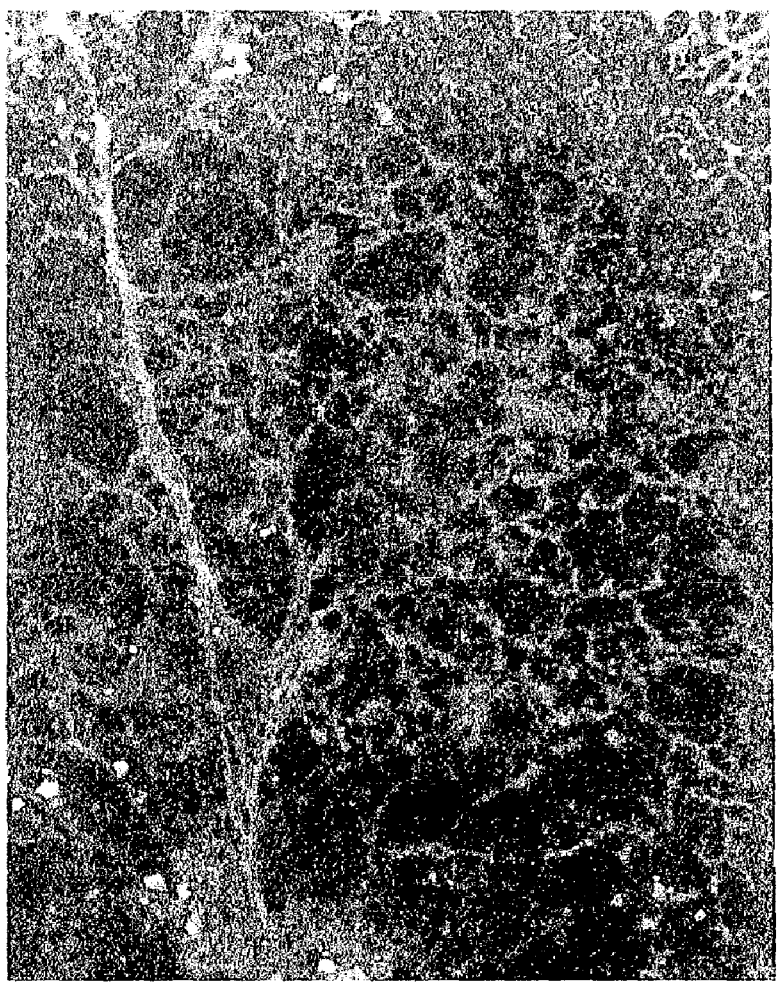
FIG. 1: Immunofluorescence studies, using anti-elastin antibodies, demonstrate the variability and complexity of the elastic fiber network produced by the rat pleural mesothelial cells.

The subject invention is directed to the treatment of tissue fibrosis by administration of an effective amount of lectin. Fibrosis herein refers to the accumulation of extracellular matrix constituents that occurs following trauma, inflammation, tissue repair, immunological reactions, cellular hyperplasia, and neoplasia. Examples of tissue fibrosis include, but are not limited to, interstitial pulmonary fibrosis, pulmonary fibrosis, cirrhosis of the liver, skin scars and keloids, adhesions, fibromatosis, atherosclerosis, and amyloidosis. The treatment is intended for a variety of mammals, including human.

Lectins which may be administered to treat tissue fibrosis include, but are not limited to, lectins which bind to N-acetylglucosamine, such as chitin-binding lectins and mannose-binding lectins.

Administration of the lectin may be performed intratracheally, intravenously, intramuscularly, topically, orally, or by any other route deemed efficacious. The lectin may be administered alone, or with a carrier such as saline solution, DMSO, an alcohol, or water. The lectin may be isolated from a natural source, such as plants or animals, or synthesized by a bioprocess, such as fermentation. The effective daily amount of lectin is from about 10 µg/kg to about 10 mg/kg of body weight.

For intratracheal administration, the amount of lectin administered daily to a human being may vary from about 10 µg/kg to about 1 mg/kg of body weight. Preferably, the daily amount is from about 10 µg/kg to about 100 µg/kg, for example about 50 µg/kg body weight of the human being treated (daily). The intratracheal lectin may be administered in any of the methods well known to those skilled in the art. For example, the lectin may be administered in the form of an aerosol or may be administered in solution via a catheter. If administered in the form of an aerosol, a nebulizer may be used to produce lectin in aerosol form (See for example U.S. Pat. Nos. 4,649,911 and 4,119,096).

Typically, the lectin is administered in a pharmaceutically acceptable carrier. Such examples include saline solution, DMSO, an alcohol, or water. Such carriers are well known in the art, and the specific carriers employed may be varied depending upon factors such as size of the subject being treated, treatment dose, and the like.

Further, the time over which the lectin is administered may vary as is well known in the art to achieve the desired results. For example, the lectin may be intratracheally administered as an aerosol for a time period of between 10 minutes and 1 hour per treatment regimen, twice daily, or until the desired daily dosage is fully administered.

The lectin may be derived from plant or animal species, or synthesized by a bioprocess, such as fermentation. All forms of lectin, regardless of source, would follow a treatment similar to that described above.

EXPERIMENTAL FINDINGS

Methods

Preparation of a Radiolabeled Cell-Free Tissue Culture Matrix:

Rat pleural mesothelial cells, obtained from the American Type Culture Collection (Rockville, Md.), were cultured in 75 cm$^2$ plastic flasks using Nutrient Mixture Ham's F-12 medium supplemented with 15% fetal bovine serum, 1% glutamine, 20 units/ml streptomycin, and 20 units/ml penicillin G. The cultures were incubated at 37° C. in a humidified atmosphere containing 5% $CO_2$. Cells and extracellular matrix were radiolabeled for 6 weeks with $^{14}$C-lysine (6.25 µCi per flask). At the end of the labeling period, the cultures were washed with phosphate-buffered saline (PBS) and the cells were lysed with 0.5% sodium deoxycholate and EGTA. Following removal of the cellular material, the matrix was rinsed with PBS and allowed to air dry. The plastic surface containing the radiolabeled matrix was then cut into 2×2 cm squares.

Identification of Matrix Elastic Fibers:

Immunohistochemical identification of elastic fibers within the matrix was performed, using a primary goat anti-rat lung alpha-elastin antibody (Elastin Products Co, Owensville, Mo.) and a secondary, fluorescein-labeled rabbit anti-goat IgG antibody (Zymed Laboratories, San Francisco, Calif.). Matrix samples, prepared from cells grown on glass slide cover-slips, were fixed in acetone, treated with goat serum for 30 min, and washed with PBS. The samples were then incubated with goat anti-rat lung elastin antiserum for 1 hr and again washed with PBS. After treatment with rabbit serum for 30 min, a secondary, fluorescein-labeled rabbit anti-goat IgG antibody (Zymed Laboratories, San Francisco, Calif.) was applied for 1 hr. The matrix samples were then washed with PBS, mounted on glass slides, and examined with a fluorescence microscope.

Fluorescein-Labeled Lectin Studies:

Matrix samples were treated with 1 mg/ml fluorescein-labeled tomato lectin (Sigma-Aldrich, St Louis, Mo.) for 30 minutes, washed with PBS, and examined with a fluorescence microscope. The resulting pattern of fluorescence was compared to that observed with the immunohistochemical studies of the matrix elastic fibers, using antielastin antibodies.

Lectin-HA Studies:

Matrix squares were overlaid with 0.5 ml of 1 mg/ml tomato lectin (Sigma Chemical Co, St Louis, Mo.) in PBS for 30 min at room temperature. Following removal of the liquid, the matrices were dried and treated with 1 mg/ml streptococcal HA (CarboMer Co., Westborough, Mass.) in 0.5 ml PBS for 30 min at room temperature After removal of the liquid, the matrices were dried and incubated for 3 hrs at 37° C. with 0.5 ml of 1.0 µg/ml or 100 ng/ml of porcine pancreatic elastase (Elastin Products Co., Owensville, Mo.) in 0.1 M Tris buffer, pH 8.0. Controls were treated with PBS instead of lectin prior to incubation with HA and elastase.

Results were expressed as net cpm per matrix square after subtracting background radioactivity released from samples only treated with PBS for 30 min and Tris buffer for 3 hrs.

Determination of Extracellular Binding Sites for Lectins:

Elastin isolated from bovine ligamentum nuchae was hydrolyzed in 6 N HCl overnight at 100° C. The hydrolysate was then evaporated to dryness, reconstituted in water and chromatographed in a system of butanol, acetic acid, and water (4:1:1). The material remaining at the origin was eluted and further purified by cellulose thin-layer plate electrophoresis. It was then eluted from the cellulose plate and subjected to $^3$H-NMR and $^{14}$C-NMR. Mass spectroscopy and elemental analysis was also performed.

Results

Lectin Binding to Extracellular Matrix:

The rat pleural mesothelial cells used in these studies were previously shown to abundantly synthesize elastin and form a matrix largely composed of elastic fibers. Immunofluorescence studies, using anti-elastin antibodies, demonstrate the variability and complexity of this fiber network (FIG. 1).

Figure 2:
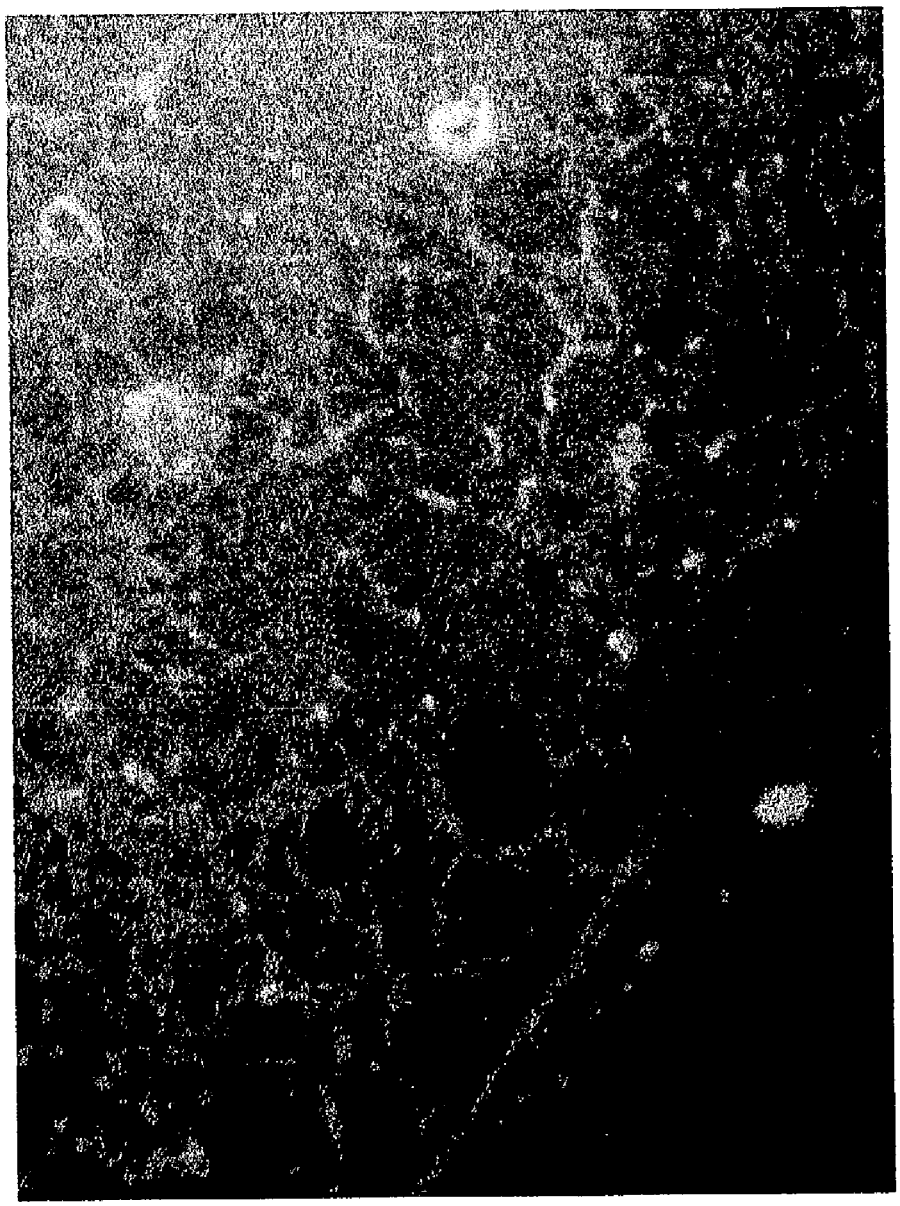
FIG. 2: Photomicrograph of fluorescein-labeled tomato lectin binding to the elastic fiber matrix.

Matrix treated with fluorescein-labeled lectin revealed a similar pattern of fluorescence, demonstrating that the lectin binds to these fibers (FIG. 2). No significant immunofluorescence was seen in matrix samples that were not treated with fluorescein-labeled lectin.

Figure 3:
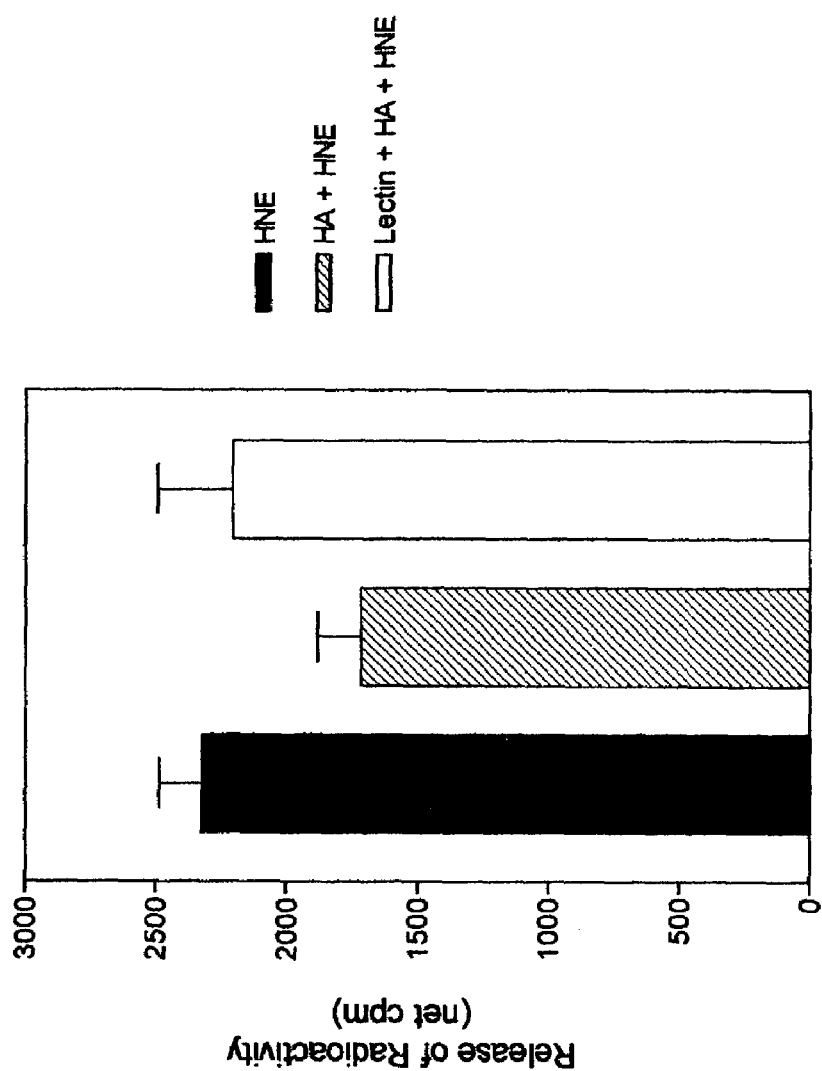
FIG. 3: Pretreatment of radiolabeled matrix with tomato lectin impairs the ability of hyaluronan to protect elastic fibers from elastase-mediated degradation, as measured by release of radioactivity.

Effect of Lectin on HA-Mediated Protection of Matrix Elastic Fibers:

Since HA was previously shown to bind to this matrix and reduce elastase injury (2), tomato lectin was tested for its capacity to alter this protective effect. As in previous studies, treatment of radiolabeled matrix with HA significantly decreased elastase-induced release of radioactivity compared to untreated controls (FIG. 3). In contrast, radiolabeled matrix exposed to lectin prior to treatment with HA did not show a similar decrease in elastolysis, but instead produced a significant increase in release of radioactivity compared to samples treated with HA alone (FIG. 3).

Figure 4:
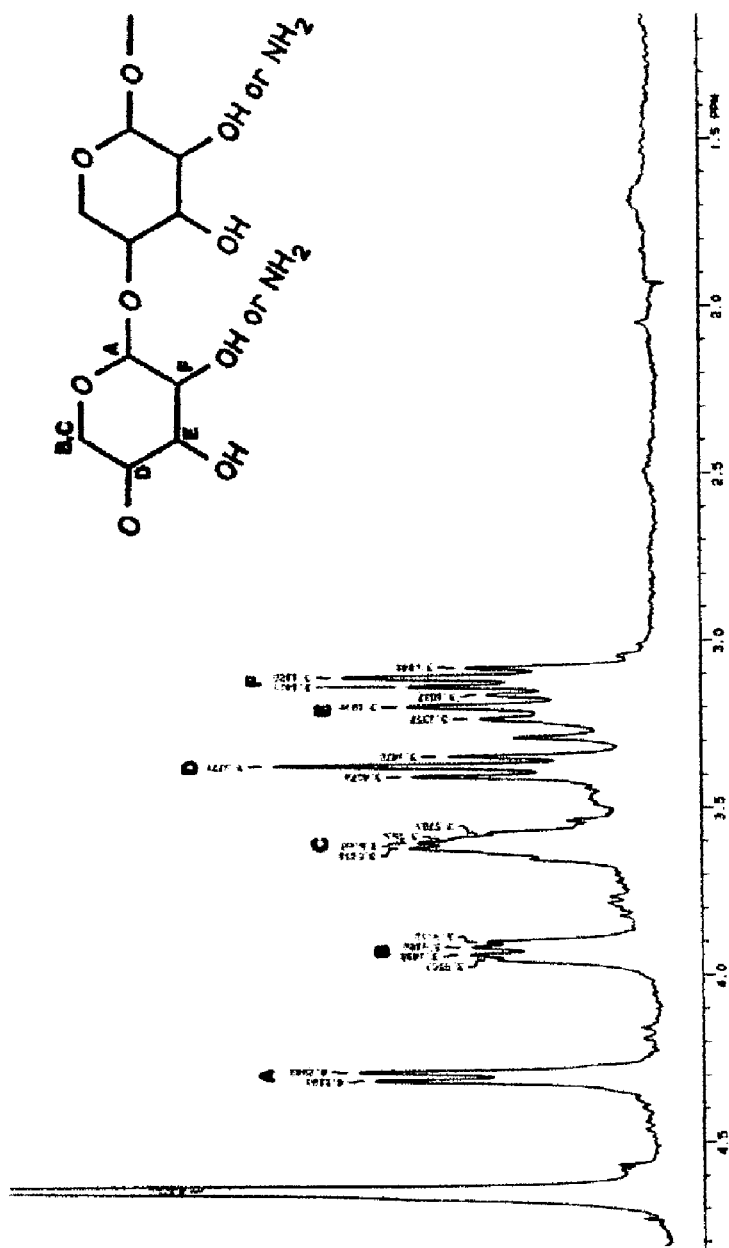
FIG. 4: Proton-NMR spectra of compound isolated from elastin.
Figure 5:
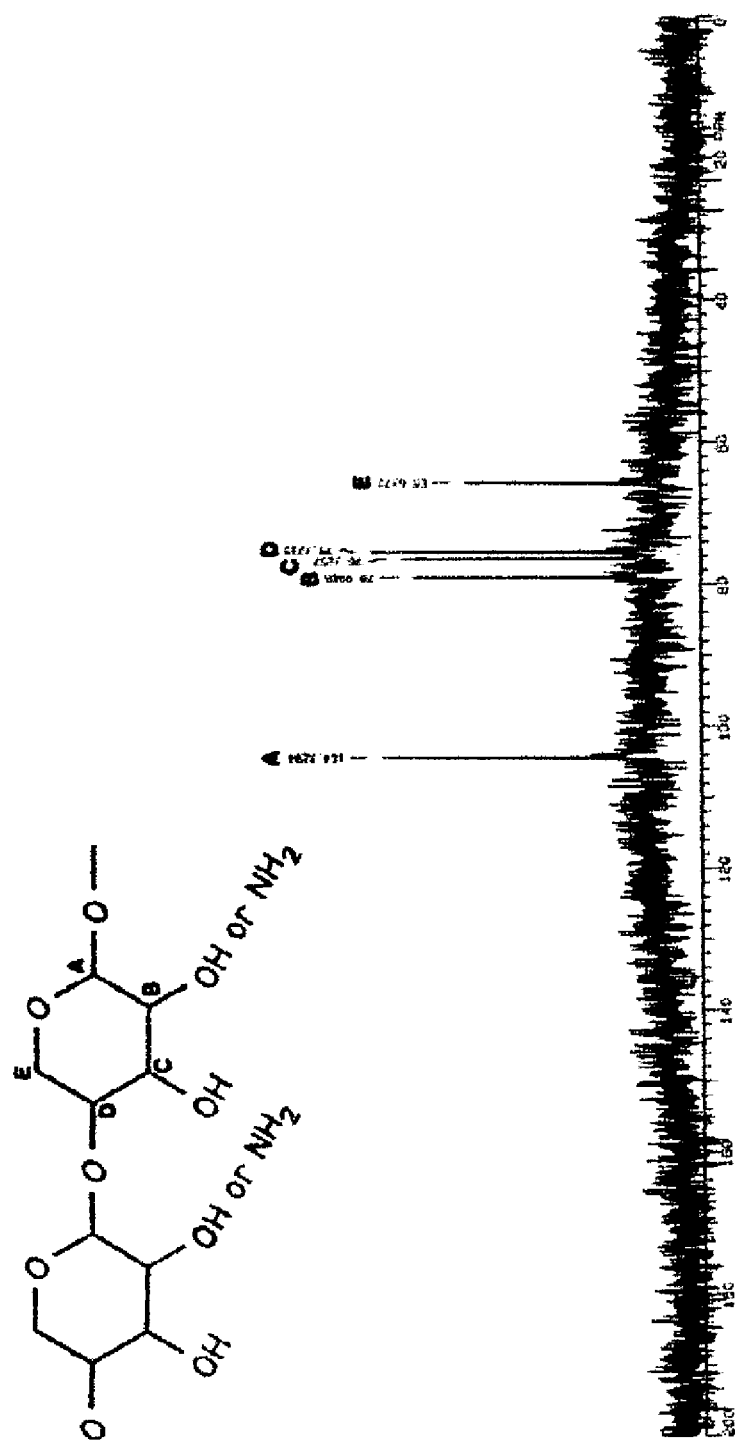
FIG. 5: Carbon-NMR spectra of compound isolated from elastin.
Figure 6:
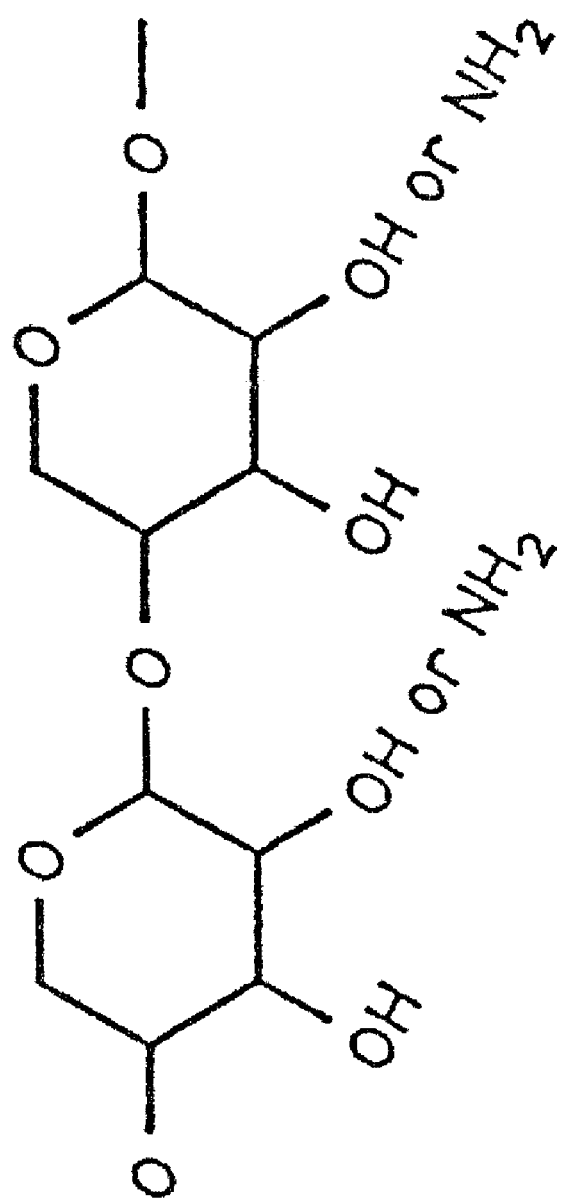
FIG. 6: Proposed structure of elastin-associated polysaccharide (classified as a glucan).

Identification of Potential Extracellular Binding Sites for Lectins:

Analysis of the NMR spectra revealed a molecule composed of repeating, nonaromatic, polyhydroxylated, 5-carbon ring units (FIGS. 4,5). The proposed molecular structure of the compound (classified as a glucan) is shown in FIG. 6. Elemental analysis yielded 44% carbon, 71% hydrogen, 45% oxygen, and 4% nitrogen, which is in good agreement with this structure. No definitive molecular weight was revealed by mass spectroscopy, consistent with the polydisperse nature of glucans. Since 1.3 mgs of purified material was isolated per gram of elastin, the compound is probably not a contaminant and may instead play an important role in the function of elastic fibers. It is speculated that the compound may be derived from the matrix surrounding elastin (possibly from the microfibrillar component) and perhaps contribute to the assembly of elastic fibers, eventually becoming integrated into elastin itself.

Discussion

While the mechanism responsible for the observed affinity of tomato lectin for elastic fibers is unclear, it is possible that this lectin may bind to specific polysaccharides in elastic fibers. Studies by this laboratory have demonstrated the presence of a glucan-like carbohydrate associated with elastic fibers (3). Glucans composed of repeating saccharide units, may conceivably be a constituent of the microfibrillar component that surrounds the elastin protein and becomes incorporated into elastic fibers.

As shown above, tomato lectin may impair the binding of hyaluronan to elastic fibers, making them more susceptible to degradation by elastases and other agents. Since hyaluronan synthesis is greatly increased during the initial stages of the fibrotic response to tissue injury (4–6), the addition of lectin to the matrix at an early time point may interfere with the subsequent accumulation and organization of newly synthesized fibrous tissue, thus preventing scar formation.

This anti-fibrotic effect may not be limited to tomato lectin, since lectins, in general, bind to carbohydrate moieties in elastin and other matrix constituents (7–9). Indeed, lectins with affinities for specific polysaccharides may ultimately be utilized to alter the composition and structural properties of the extracellular matrix.

REFERENCES

1. Cantor J O, Wilhite M, Bray B A, Keller S, Mandl I, Turino G M. Synthesis of crosslinked elastin by a mesothelial cell culture. Proc Soc Exp Biol Med 181: 387–391, 1986.
2. Cantor J O, Shteyngart B, Cerreta J M, Liu M, Armand G, Turino G M. The effect of hyaluronic acid on elastic fiber injury in vitro and elastase-induced airspace enlargement in vivo. Proc Soc Exper Biol Med:225:65–71, 2000.
3. Cantor J O, Manahan J, Keller S, Armand G, Moret J, Turino G M. Structural characterization of a new elastin-related compound. Amer Rev Respir Dis 145:A825, 1992.
4. Hemnas J, Mettelbladt O, Bjerner L, Samstrand B, Maimstrom A, Haligren R. Alveolar accumulation of fibronectin and hyaluronan precedes bleomycin-induced pumonary fibrosis in the rat. Eur Respir J 5:404–410, 1992.
5. Nilsson K, Henriksson R, Helistrom S, Tengblad A, Bjermer L. Hyaluronan reflects the pre-fibrotic inflammation in irradiated rat lung: concomitant analysis of parenchymal tissues and bronchoalveolar lavage. Int J Radiat Biol 58:519–530,1990.
6. Nettelbladt O, Bergh J, Schenholm M, Tengblad A, Haligren R. Accumulation of hyaluronic acid in the alveolar interstitial tissue in bleomycin-induced alveolitis. Am Rev Respir Dis 139:759–762, 1989.
7. Palmer K G, Bale L A: Ultrastructural localization of Helix pomatia lectin-binding sites in mouse lung elastic fibers. Histochemistry 1987; 88:91–95.
8. Baba T, Takagi M, Yagasaki H: Ultrastructural cytochemistry of carbohydrates in microfibrils associated with the amorphous elastin in the monkey aorta. Anat Rec 1985; 213:385–391.
9. Cerra R F, Haywood-Reid P L, Barondes S H: Endogenous mammalian lectin localized extracellulary in lung elastic fibers. J Cell Biol 1984; 98:1580–1589.

What is claimed is:

1. A method of treating fibrosis in mammalian tissue comprising administration of an effective amount of a lectin that binds to at least one compound selected from the group consisting of galactose, fucose, n-acetyl-glucosamine, n-acetyl-galactosamine and glycosaminoglycans, wherein the method of administration is selected from the group consisting of oral, intratracheal, intravenous, or intramuscular.

2. A method of claim 1, wherein the lectin is a tomato lectin.

3. A method of claim 1, wherein the lectin is administered with one of the following carriers: saline solution, alcohol, or DMSO.

4. A method of claim 1, wherein the mammalian tissue is a human tissue.

5. A method of claim 1, wherein the fibrosis is associated with pulmonary fibrosis, cirrhosis of the liver, skin scars or keloids, adhesions, fibromatosis, atherosclerosis, amyloidosis, tissue injury, hyperplasia, or neoplasia.

6. A method of claim 1, wherein the lectin is from a plant or animal.

* * * * *